US010036745B2

(12) United States Patent
Inganäs et al.

(10) Patent No.: US 10,036,745 B2
(45) Date of Patent: Jul. 31, 2018

(54) METHOD AND KIT FOR ANALYTE DETERMINATION AT ACIDIC CONDITIONS

(71) Applicant: GYROS Patent AB, Uppsala (SE)

(72) Inventors: Mats Inganäs, Uppsala (SE); Pirjo Lehtonen, Uppsala (SE)

(73) Assignee: GYROS Patent AB, Uppsala (SE)

( * ) Notice: Subject to any disclaimer, the term of this patent is extended or adjusted under 35 U.S.C. 154(b) by 493 days.

(21) Appl. No.: 14/433,276

(22) PCT Filed: Oct. 3, 2013

(86) PCT No.: PCT/SE2013/051161
§ 371 (c)(1),
(2) Date: Apr. 2, 2015

(87) PCT Pub. No.: WO2014/055025
PCT Pub. Date: Apr. 10, 2014

(65) Prior Publication Data
US 2015/0268238 A1  Sep. 24, 2015

(30) Foreign Application Priority Data

Oct. 3, 2012  (SE) .................................. 1251116-8
Mar. 25, 2013  (SE) .................................. 1350373-5

(51) Int. Cl.
*G01N 33/537* (2006.01)
*G01N 33/543* (2006.01)
*G01N 33/53* (2006.01)

(52) U.S. Cl.
CPC ... *G01N 33/54393* (2013.01); *G01N 33/5306* (2013.01); *G01N 33/5375* (2013.01); *G01N 2333/195* (2013.01)

(58) Field of Classification Search
None
See application file for complete search history.

(56) References Cited

U.S. PATENT DOCUMENTS

| 4,703,001 | A  |   | 10/1987 | Vodian et al. |
| 4,752,571 | A  |   | 6/1988  | Berglund et al. |
| 5,420,016 | A  | * | 5/1995  | Boguslaski ............... C12Q 1/04 106/2 |
| 2004/0009178 | A1 | * | 1/2004  | Bowdish ................ C07K 16/08 506/9 |
| 2005/0179901 | A1 | * | 8/2005  | Ostlin ............... B01L 3/502715 356/445 |
| 2006/0194950 | A1 |   | 8/2006  | Hober et al. |
| 2008/0125454 | A1 | * | 5/2008  | Bedard ................ A61K 31/473 514/292 |
| 2011/0045510 | A1 |   | 2/2011  | Lang et al. |
| 2012/0052514 | A1 |   | 3/2012  | Allen et al. |

FOREIGN PATENT DOCUMENTS

| EP | 0213093 A1 | 3/1987 |
| JP | 2003279577 A | 10/2003 |
| JP | 2004529333 A | 9/2004 |
| JP | 2010503854 A | 2/2010 |
| JP | 2012502292 A | 1/2012 |
| WO | WO-9110911 A1 | 7/1991 |
| WO | WO-2008033073 A1 | 3/2008 |
| WO | WO-2009022001 A1 | 2/2009 |
| WO | WO-2012154253 A1 | 11/2012 |
| WO | 2013/121368 A2 | 8/2013 |

OTHER PUBLICATIONS

Diamandis et al., Immunoassay, The Avidin-Biotin System, Chapter 11, pp. 237-255, 1996. (Year: 1996).*
Sickert et al., "Improvement of drug tolerance in immunogenicity testing by acid treatment on Biacore", Journal of Immunological Methods, 2008, vol. 334, pp. 29-36.
Knicker et al., "Immunoassay to measure staphylococcal protein A in the presence of murine immunoglobulins", Journal of Immunological Methods, 1991, vol. 142, pp. 53-39.
Aggarwal, "What's fueling the biotech engine—2010-2011", Nature Biotechnology, vol. 29, No. 12, 2011, pp. 1083-1089.
Chon et al., "Advances in the production and downstream processing of antibodies", New Biotechnology, vol. 28, No. 5, 2011, pp. 458-463.
F-D-C Reports, "The Gold Sheet—Pharmaceutical & Biotechnology Quality Control", vol. 38, No. 9, 2004, pp. 1-32.
Forsgren et al., "Protein A From *S. aureus*: I. Pseudo-Immune Reaction with Human γ-Globulin", J. Immunol., vol. 97, No. 6, 1966, pp. 822-827.
Inganäs, "Comparison Between Mechanisms of Interaction between Protein A from *Staphylococcus aureus* and Human Monoclonal IgG, IgA, and IgM in Relation to the Classical Fcγ and the Alternative $F(ab')_2^E$ Potein A Interactions", Scand. J. Immunol., No. 13, 1981, pp. 343-352.
Jansson et al., "All individual domains of staphylococcal protein A show Fab binding", FEMS Immunology and Medical Microbiology, No. 20, 1998, pp. 69-78.
Lindahl et al., "Autoantibodies to cardiac troponin in acute coronary syndromes", Clinica Chimica Acta, No. 411, 2010, pp. 1793-1798.
Murphy et al., "Progress in matrix metalloproteinase research", Mol Aspects Med., No. 29(5), 2008, pp. 290-308.
Nilsson et al., "A synthetic IgG-binding domain based on staphylococcal protein A", Protein Engineering, vol. 1, No. 2, 1987, pp. 107-113.

(Continued)

*Primary Examiner* — Gary Counts
(74) *Attorney, Agent, or Firm* — Norton Rose Fulbright US LLP

(57) ABSTRACT

A method of quantitatively determining an analyte in a fluid sample by an immunoassay comprises binding of the analyte to a ligand capable of specifically binding to the analyte, wherein at least part of the analyte is present as an analyte complex is disclosed. The method comprises the steps of: a) subjecting the sample to a first acidic pH to at least substantially dissociate any analyte complex present and provide substantially all analyte in free form, b) raising the first acidic pH to a second acidic pH where re-formation of complexes is prevented but where binding of analyte to the ligand is permitted, and c) determining the binding of analyte to the ligand to quantitatively determine the analyte in the sample.

12 Claims, 11 Drawing Sheets

(56) References Cited

OTHER PUBLICATIONS

Reuschenbach et al., "A systematic review of humoral immune responses against tumor antigens", Cancer Immunol. Immunother., No. 58(10), 2009, pp. 1535-1544.

Slemmon et al., "Measurement of Aβ1-42 in cerebrospinal fluid is influenced by matrix effects", Journal of Neurochemistry, No. 120, 2012, pp. 325-333.

Starovasnik et al., "Antibody variable region binding by Staphylococcal protein A: Thermodynamic analysis and location of the Fv binding site on E-domain", Protein Science, No. 8, 1999, pp. 1423-1431.

Steindl et al., "A simple method to quantify staphylococcal protein A in the presence of human or animal IgG in various samples", Journal of Immunological Methods, No. 235, 2000, pp. 61-69.

Zhu-Shimoni et al., "Trace level analysis of leached Protein A in bioprocess samples without interference from the large excess of rhMAb IgG", Journal of Immunological Methods, No. 341, 2009, pp. 59-67.

\* cited by examiner

METHOD AND KIT FOR ANALYTE DETERMINATION AT ACIDIC CONDITIONS

CROSS-REFERENCE TO RELATED APPLICATIONS

This application is a national phase application under 35 U.S.C. § 371 that claims priority to PCT Application No. PCT/SE2013/051161 to Gyros Patent AB filed Oct. 3, 2013, which claims the benefit of priority to Sweden Patent Application Nos. 1350373-5 filed on Mar. 25, 2013 and 1251116-8 filed on Oct. 3, 2012, all of which are incorporated herein by reference in their entirety.

FIELD OF THE INVENTION

The present invention relates to the determination of total concentration of analyte in fluid samples wherein the analyte may at least partially be in complex form, typically as an immune complex. More particularly, the invention relates to an assay method where preformed analyte complexes are dissociated prior to determining the analyte, as well as a kit for performing the method.

BACKGROUND OF THE INVENTION

In order to reliably perform immunoassays, unrestricted access to selected epitopes on target molecules, or analytes, as defined by selected antibodies, are necessary for quantitative determination of the analytes. If two or more different proteins, capable of interacting with each other under physiological conditions, have formed complexes, the component at lower concentration will, depending on the interaction properties and concentrations of the two interactants, partly appear in complexed form with the counterpart. This may prove disadvantageous for quantification particularly of the counterpart in lower concentration as some epitopes used for the assay might be hidden in the complex.

Certain types of proteins may form homo-multimers, e.g. fibrillating proteins, where critical epitopes essential for assaying will not be fully accessible in protein aggregates. If the monomer has a limited number of epitopes this might contribute to underestimation of the monomer protein concentration when multimerization is prone to occur (1).

In order to preserve homeostasis, protein complexes may be formed between active enzymes and their inhibitors in a pre-determined ratio complicating accurate determination of the enzyme. This may lead to certain epitopes being inaccessible in immunoassays and hence an immunoassay may generate inaccurate concentration estimates (2).

Intermittent release of intracellular proteins over longer periods of time due to cell damage of e.g. cardiac cells (3) or tumour cells (4) may generate immune responses against intracellular proteins. These may in a later stage contribute to the formation of immune complexes composed of target molecules and auto-antibodies. Given the amplification properties of the immune system, antibodies may be formed at much higher relative concentrations compared to the target protein leading to formation of immune complexes complicating accurate quantification of target protein.

The above examples represent situations where quantification of target analyte may generate significant deviations from the true target analyte value, often greatly underestimating the true concentration.

Also in biochemical purification processes similar phenomena may occur. In recent years a whole new class of therapeutics, recombinant monoclonal antibodies, has been introduced for treatment of various disorders such as inflammatory diseases, cancer and infection (5). Many of the original therapeutic monoclonal antibodies are purified from cell culture by sequential purification steps employing affinity chromatography, ion exchange chromatography and possibly gel filtration (6). Quite commonly the affinity purification step is based on the interaction between IgG and protein A from *Staphylococcus aureus*. Protein A immobilized to suitable resins is used as a capturing agent for cell culture containing monoclonal antibodies. This step is very efficient in enriching the desired molecule while contaminants from the cell culture are significantly reduced.

Unfortunately, the ligand used for purification may leach from the resin during the process and end up as an impurity in the purified material. Leaching may occur as a consequence of the dissociation conditions used, for example, proteolytic cleavage of ligand by components from the cell culture, but also the property of resins used, the immobilization chemistry and other aspects related to manufacturing of the affinity resin, as well as the forces involved in the bio-specific interaction between the interactants, may all contribute to ligand leaching to some degree. Irrespective of which specific mechanism is involved, the ligand may contaminate the product being purified on the affinity resin. Depending on the specific biological properties of the impurity ligand, administration of therapeutic proteins purified according to these principles, which may contain biologically active impurities, may induce non-desired side effects, e.g. allergic shock or complement activation, increasing the risk-profile of the treatment.

Native protein A, produced by staphylococci, interacts with immunoglobulins in two principally different manners:
 The classical interaction involving the Fc portion of human IgG (7).
 The alternative interaction involving immunoglobulins, irrespective of immunoglobulin class (8), that belongs to the $V_H III$ (9) group of the variable domain of the heavy chains.

Native protein A has five immunoglobulin binding domains (10), each of which can interact independently with IgG portions Fcγ and Fab, respectively. This creates a multitude of interaction possibilities between IgG and protein A, even forming precipitates at equimolar proportions (7). However, it is likely that also under conditions when the proportions of interactants are very dissimilar, heterogeneous complexes will be formed engaging several of the potential interactions in complex formation.

Native protein A has been modified using recombinant technologies (11). One example is when native, staphylococcal protein A or recombinant versions of the same molecule, Fragment Z in multimer version (11), or MabSelect SuRe™ ligand (GE Healthcare Life Sciences, Uppsala, Sweden), a protein A-derived molecule and modified with respect to alkaline tolerance (12) (immobilized on agarose in chromatography medium MabSelect SuRe™) to improve stability upon repeated cleaning-in-place procedures, are used as ligand in the purification process. Thus, during the purification procedure native protein A or its recombinant relatives, respectively, may leach from the resin and form complexes with the eluted IgG once buffer conditions during the continued purification process reach a pH allowing complex formation between protein A and IgG. Attempts to quantify the amount of protein A in relation to IgG expressed as ppm in neutral pH are likely to be severely affected by limited access to relevant epitopes on protein A. This is likely to lead to underestimation of the real concentration of protein A. In order to avoid patient exposure for too high concentrations of leached protein A these levels should be less than 12-14 ppm (13).

Two different principles have been applied to disrupt protein A-IgG complexes to make protein A accessible for quantification:

Heat denaturation of the IgG component present in the sample used for quantification of protein A in the presence of compounds assisting in the denaturation process (14). Protein A is considered to resist denaturation from such treatment. Once the IgG component of the complex is denatured the process will release the protein A moiety for accurate quantification (15).

Acid treatment of sample to dissociate preformed complexes and performance of immunoassay under acid conditions (16; WO 91/10911). Here immune reagents used in the immunoassay must tolerate the selected acid conditions. Optimally the selected pH should, on the one hand, quantitatively dissociate complexes between protein A and IgG (i.e. dissociate protein A from the Fc and/or Fab regions) while, on the other hand, the assay is still functional, a combination that has proven difficult to fulfill.

In many cases heat denaturation is not feasible. One example is when using an analytical system of a type exemplified by the Gyrolab™ system (Gyros AB, Uppsala, Sweden) where assays are performed in microfluidic structures provided in a spinnable compact disc (CD). Firstly, the heat treatment of the sample would have to be performed outside the CD and the instrument as there is no heating mechanism available therein. Secondly, it is likely that intra-CD heat treatment would destroy critical functions incorporated in the CD, potentially also generating protein aggregates which are incompatible with microfluidic-based assay principles. When heating is performed outside the CD, it is possible that protein particulates might be formed with the risk of clogging microstructures unless appropriate precautions are taken.

WO 2008/033073 A1 discloses a method of determining the total concentration of an analyte in a fluid sample, wherein at least part of the analyte is present as a complex with an analyte-binding species. The method comprises the steps of: a) subjecting the sample to conditions that reduce the binding affinity between analyte and analyte-binding species sufficiently to dissociate substantially any analyte complex and provide substantially all analyte in free form, b) subjecting the sample to conditions that restore the binding affinity between analyte and analyte-binding species, and c) immediately after the binding affinity has been restored, and before any substantial re-complexing of the analyte has taken place, determining the concentration of free analyte in the sample. In one embodiment, the method is performed in a flow system using label-free detection, such as surface plasmon resonance (SPR).

WO 2009/022001 A1 discloses a method based on surface plasmon resonance for detection of anti-drug antibodies (ADAs) against a therapeutic drug. Drug interference in the presence of drug in the patient sample to be analysed is overcome by acidifying the sample (pH 2.5 or 3), and then neutralizing the sample before analysis.

It is an object of the present invention to provide a method for quantifying total analyte in a sample, including analyte in complexed form, which is based on complex dissociation by acid treatment and which is generally functional for a variety of analytes and capturing agents, especially antibodies.

SUMMARY OF THE INVENTION

The above-mentioned object is achieved by an improved method wherein separate acidic pH's are used for, on the one hand, dissociating preformed complexes (e.g. protein A-IgG complexes) in fluid samples and, on the other hand, performing the immunoassay, viz. at a pH where reformation of complexes is largely prevented, and at which the capture molecule, typically antibody, is sufficiently active to generate a dose response for the analyte, even in presence of large amounts of complexing component.

In one aspect, the present invention therefore provides a method of quantitatively determining an analyte in a fluid sample by an immunoassay comprising binding of the analyte to a ligand capable of specifically binding to the analyte, wherein at least part of the analyte is present as an analyte complex, and wherein the method comprises the steps of:

a) subjecting the sample to a first acidic pH to at least substantially dissociate any analyte complex present and provide substantially all analyte in free form, b) raising the first acidic pH to a second acidic pH where re-formation of complexes is (at least largely) prevented but where binding of analyte to the ligand is permitted, and c) determining the binding of analyte to the ligand to quantitatively determine the analyte in the sample.

The term "analyte complex" as used herein includes complexes with specifically as well as non-specifically binding species, and also includes multimers, such as dimers or trimers, of the analyte.

The ligand may, for example, be an antibody. The term "antibody" as used herein is to be interpreted in a broad sense and refers to an immunoglobulin which may be natural or partly or wholly synthetically produced and also includes active fragments, including Fab antigen-binding fragments, univalent fragments and bivalent fragments. The term also covers any protein having a binding domain which is homologous to an immunoglobulin binding domain. Such proteins can be derived from natural sources, or partly or wholly synthetically produced. Exemplary antibodies are the immunoglobulin isotypes and the Fab, Fab', F(ab')2, scFv, Fv, dAb, and Fd fragments.

Typically, the ligand is immobilized to a solid support.

In one embodiment, the analyte is selected from protein A, protein G, protein A/G, protein L or derivatives thereof (including native variants and recombinantly produced proteins or polypeptides), and the sample contains IgG.

In another embodiment, the first acidic pH is selected in the range from about 1.5 to about 3.2 (especially 1.5 to 3.2), and the second acidic pH is selected in the range from about 2.7 to about 4.5 (especially 2.7 to 4.5), more preferably from about 2.8 to about 4.5 (especially 2.8 to 4.5). The second acidic pH may, for example, be selected in the range of from about 3.0 to about 4.5 (especially 3.0 to 4.5).

In one embodiment, the first acidic pH is selected in the range from about 2.3 to about 2.5 (especially 2.3 to 2.5) and/or the second acidic pH is selected in the range from about 2.8 to about 3.2 (especially 2.8 to 3.2). Alternatively, the second acidic pH is selected in the range from about 3.3 to about 3.5 (especially 3.3 to 3.5) or from about 3.0 to about 3.2 (especially 3.0 to 3.2).

The method may conveniently be performed in a microfluidic system.

Another aspect the present invention provides a kit for performing an immunoassay of an analyte which is present in a fluid sample at least partially in complex form, comprising:
- a detection reagent capable of binding to the analyte,
- a first acidic buffer, preferably having a pH in the range from about 1.5 to about 3.2, and
- a second acidic buffer having a higher pH than the first acidic buffer, preferably a pH in the range from about 2.7 to about 4.5.

In one kit embodiment, the analyte is capable of binding to a ligand immobilized to a solid phase, and the kit further comprises a capture reagent for the analyte, wherein the capture reagent is capable of binding to the solid phase.

Preferably, the capture reagent is biotinylated and the ligand is avidin or streptavidin.

Other preferred embodiments are set forth in the dependent claims.

A more complete understanding of the invention, as well as further features and advantages thereof, will be obtained by reference to the following detailed description and drawings.

For simplicity and brevity, the term "MabSelect SuRe™ ligand" will in the following frequently be referred to as "MabSelect SuRe".

DETAILED DESCRIPTION OF THE INVENTION

Figure 1:
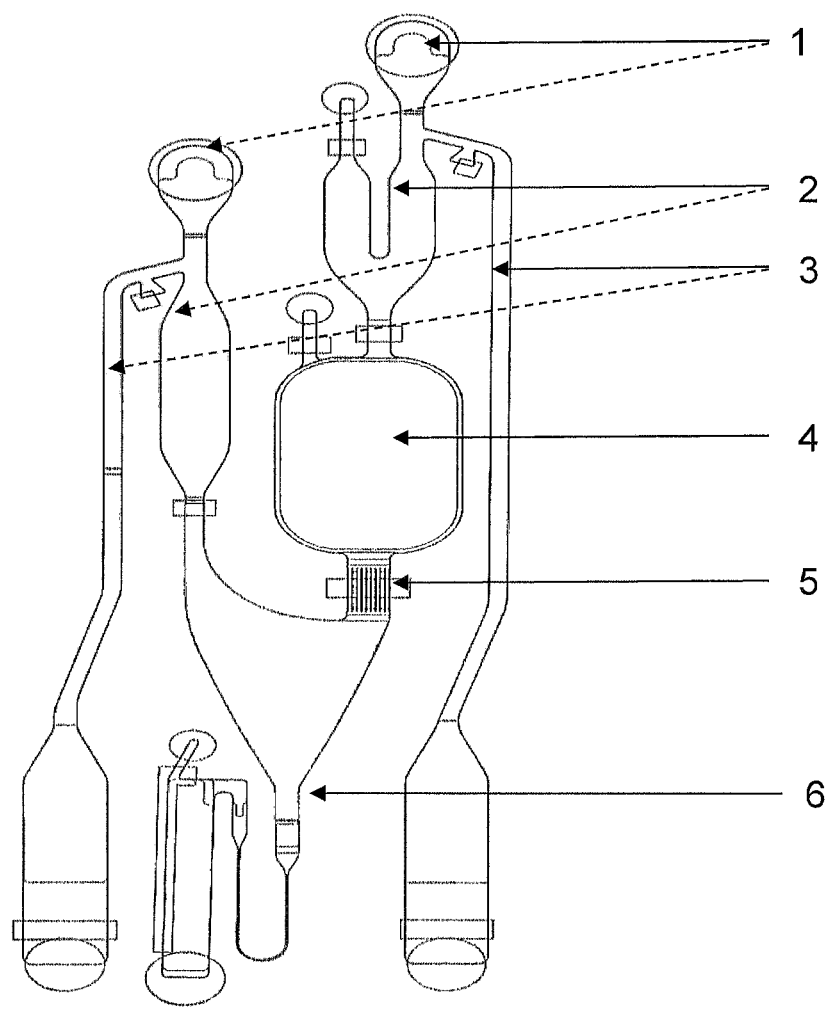
FIG. 1 is a plan view of a microstructure for performing an embodiment of the method of the present invention.

As mentioned above, the present invention is based on the principle of using separate acidic pH's for the dissociation of preformed complexes in a sample and for performing the immunoassay, and more specifically by first using a relatively low pH for efficient complex dissociation, and subsequently performing the assay at a higher acidic pH where restoration of complexes is largely prevented, while the capture agent (typically antibody) is sufficiently active for efficient capture of the analyte to be quantified.

The method may be performed using a wide variety of assay systems and assay formats.

Preferably, a heterogeneous assay system comprising a solid support surface with an immobilized analyte-specific ligand is used for measuring analyte concentration by detecting directly or indirectly the amount of binding to the solid support surface, either of the analyte (direct assay, including sandwich assay; or displacement assay) or of a detectable analyte analogue (competition assay). The solid support surface may have a variety of shapes as is per se known in the art and may, for example, be particles in a packed bed, typically provided in a microfluidic channel or cavity; or may be a surface area of a cuvette or well, such as a micro-well or a flow cell or channel, or the like.

While the method of the invention is generally applicable to a wide variety of analytes and analyte complexes, it will in the following be described primarily with regard to the quantification of protein A and protein A derivatives in the presence of IgG in a liquid sample, and with regard to performing the assay in a microfluidic system specifically the above-mentioned Gyrolab™ platform.

Examples of other analytes when present at least partially in complex form that may be contemplated for determination by the method of the invention include:
- Troponin I which is dissociated from IgG autoantibody in analysis of Troponin I.
- Dissociation of autoantibody against cancer antigen in determination of antibody when screening for cancer.
- Dissociation of homomer (aggregates and fibrils) of Amyloid beta when determining Amyloid beta.
- Dissociation of enzyme/enzyme inhibitor in determination of enzyme by immunochemical methodology, e.g. dissociation of metalloproteases/TIMP inhibition.

As mentioned in the background section, it has previously been suggested to use a selected acidic pH for the complex dissociation and to perform the immunoassay at the same pH. In the inventors' experience it is difficult to completely eliminate the quantitative implications of inefficient dissociation of preformed protein A-IgG complexes using one selected pH for dissociation and quantification, at least with currently available immunoreagents used in the assay.

However, it was also noted that in some cases, the selected pH for immunoassay is efficient for preventing the formation of complexes, e.g. when IgG and protein A solutions are acidified before being mixed, a situation which of course is quite far from the real analytical situation. However, this observation fits with basic biochemical principles demonstrating "hysteresis effects" on the conditions required for, on the one hand, dissociating pre-formed complexes and, on the other hand, the conditions required for preventing complex re-formation (17). Thus it takes more energy to dissociate preformed complexes than preventing the formation of new complexes.

The present invention is based on transferring the above observations into practice, i.e. that it would be attractive to quantitatively dissociate complexes at a first low pH, and perform the assay at a second higher acidic pH, which is compatible with functional properties of the antibodies used, but selected such that re-formation of complexes is prevented (at least to a substantial degree). It should be emphasized that performing immunoassays at a mildly acidic pH, such as 3.5, is still very demanding on most antibodies. The present invention takes advantage of the hysteresis seen in interactions between molecules displaying natural affinity and of which at least one of the counterparts is subject to quantification using immunoassay.

The method of the invention will now be described in the context of being used with a Gyrolab™ immunoassay platform (Gyrolab AB, Uppsala, Sweden). The Gyrolab™ system, or workstation, uses compact discs (CD) with a plurality of microfluidic structures. For more detailed information on this type of microfluidic analytical technology it may be referred to, for example, WO 99/058245, WO 02/074438 A2, WO 02/075312 A1, WO 03/018198 A1, WO 2004/083108 A1 and WO 2004/083109 A1 (the relevant disclosures of which are incorporated by reference herein).

FIG. 1 illustrates one of the microstructures of Gyrolab™ CD, CDMX1, containing two liquid inlets (1), two volume definition units (2), an overflow channel (3), a mixing chamber (4), an enforced finger valve (5), and a capture column (6) where reactions take place and which contains beads coupled with ligand, here typically streptavidin to be coupled to biotinylated capture antibody (the streptavidin-biotin interaction is stable in the acid pH conditions used in the present method). A hydrophobic barrier (not shown) separates the mixing chamber (4) from the capture column (6). Reagents and buffers for performing the immunoassay are introduced in the left inlet (1), and samples and reagents for sample pre-treatment are introduced in the right inlet (1). The mixing chamber (4) is located upstream of the capture column (6), i.e. spinning of the CD will cause liquid to flow from the mixing chamber (4) to the capture column (6).

Figure 2:
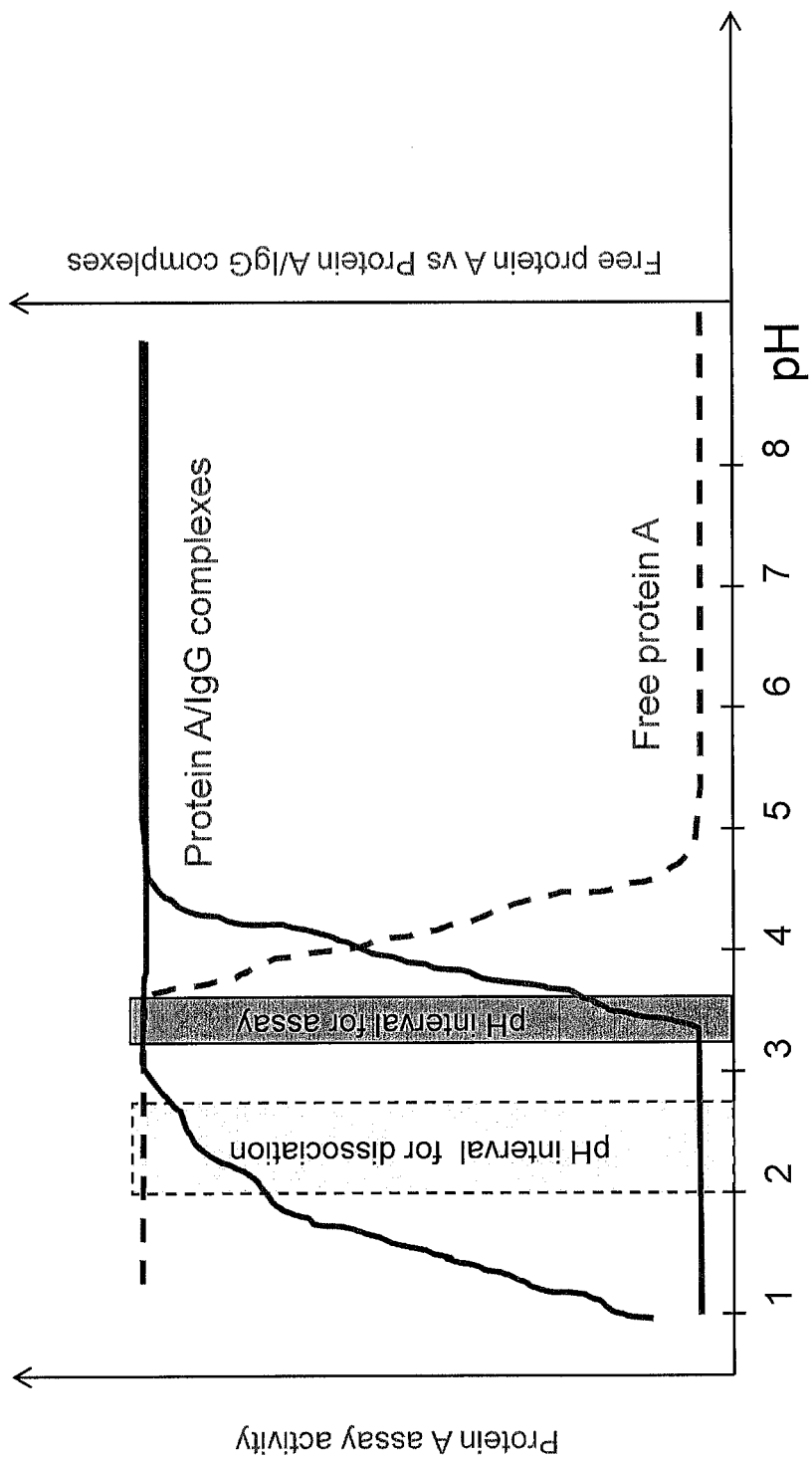
FIG. 2 is an illustration of pH intervals for protein A/IgG complex dissociation and analysis of released protein A, respectively.

Aliquots of sample and buffers aimed for pre-treatment of sample can sequentially be added in portions of, typically, 200 nl after volume definition within the CD into the mixing chamber (4). In principle any type of liquid compatible with the microfluidic principles can be added. By first introducing sample that is subsequently mixed with a selected acid buffer with appropriate buffer capacity, thereby drastically changing the pH of the mixture, preformed complexes of protein A and IgG are effectively dissociated. In the next step, another buffer is added aimed at raising the pH in the direction towards neutral pH, but only to a pH at which re-formation of complexes is fully prevented, a pH which can be tolerated by the immunoassay. Typically buffers aimed for efficient dissociation will generate a resulting pH of 1.5 to 3.2, whereas buffers intended to prepare samples for analysis will generate a resulting pH of 2.7 to 4.5, or more specifically 2.8 to 4.5, e.g. 3.0-4.5, depending on the nature of interactants, concentrations of interactants and the tolerability vs acid pH of the reagents used for the assay. These principles are schematically illustrated in FIG. 2, which shows exemplary pH intervals for protein A/IgG complex dissociation, and analysis of released protein A at mildly acidic pH preventing re-association of protein A-IgG complexes.

The dissociating effect of acid buffer addition is usually very rapid. In the protein A-IgG system, it seems that the dissociation is quantitative after 1-5 min generating a resulting pH of 2.5. The next step of adjusting the pH of the sample to running conditions for the assay is also very rapid.

The analysis step is initiated by increasing the spinning speed of the CD to overcome the resistance of the hydrophobic barrier separating the mixing chamber (4) from the capture column (6) (FIG. 1). The capture column is functionalized with an appropriate capture antibody and the capture column may have to be prewashed with the same buffer composition as the sample to prevent any momentary re-formation of protein A-IgG complexes. Once the sample has been processed through the capture column, it may have to be washed with acid buffer 2-4 times at the same pH as the sample to prevent reformation of protein A-IgG complexes, now between protein A captured on the column and any remaining IgG present in the microfluidic paths utilized during processing. Eventually, before addition of detecting reagent, the pH of the capture column is elevated to neutral to facilitate the formation of a sandwich immunoassay. The process is finalized by necessary column washes prior to detection.

EXPERIMENTAL PART

Materials and Preparation of Reagents
Capture antibodies
A polyclonal chicken anti-Protein A antibody was purchased from Cygnus Technologies, Southport, N.C., U.S.A. (www.cygnustechnologies.com). Aliquots of the antibody were labelled with biotin using EZ-link Sulpho NHS-LC-Biotin (21338, Thermo Scientific, Rockford, Ill., USA—www.piercenet.com) according to the manufacturer's instructions. Rexxip™ ADA buffer was used (Gyros AB, Uppsala, Sweden).

A biotinylated mouse monoclonal antibody directed against protein A was purchased from Sigma-Aldrich, St. Louis, Mo., U.S.A. (cta no B3150; www.sigmaaldrich.com).

A proprietary polyclonal antibody directed against protein A and designed to sustain low pH conditions was provided. An aliquot of the antibody was labelled with biotin using EZ-link Sulpho NHS-LC-Biotin (21338, Thermo Scientific).

Detection Antibodies
Aliquots of the anti-Protein A antibody from Cygnus Technologies and the proprietary anti-Protein A antibody, respectively, described under the heading "Capture antibodies" above, were labelled with a fluorophore using Alexa Fluor™ 647 (A20186, Life Technologies, Carlsbad, Calif., U.S.A.) according to the manufacturer's instructions. Rexxip™ ADA buffer was used (Gyros AB, Uppsala, Sweden).

IgG
Polyclonal human IgG (hIgG) for intravenous administration, Octagam™ (Octapharma AB, Stockholm Sweden), 50 mg/ml, was purchased from the pharmacy on prescription. This preparation is purified by alcohol fractionation and has never been in contact with protein A or any derivative of protein A.

Humira™ (a therapeutic antibody, marketed by Abbott Laboratories, Abbott Park, Ill., USA) was purchased from the pharmacy on prescription.

Herceptin™ (a therapeutic antibody, marketed by F. Hoffmann-La Roche Ltd, Basel, Switzerland) was purchased from the pharmacy on prescription.

Buffers

Buffers were prepared from solid chemicals at appropriate buffer capacity and pH.

Protein A

Protein A (native, 17-0872-05) and derivatives thereof (MabSelect SuRe™ ligand, 28-4018-60) were purchased from GE Healthcare Life Sciences, Uppsala, Sweden (www.gelifesciences.com).

CDs

CDMX1 (P0020026), also called "Gyrolab ADA CD", was from Gyros AB, Uppsala, Sweden (www.gyros.com). Column packing was (15 μm) streptavidin-derivatised Dynospheres™ (Invitrogen Dynal A.S., Oslo, Norway).

Preparation of Samples

Standard curves were prepared by dilution of protein A in 5 mg/ml of polyclonal IgG in PBS, pH 7.4, allowing complexes between protein A and IgG to be formed.

Quality control (QC) samples were prepared in separate dilutions with known concentrations of protein A in the presence of polyclonal or monoclonal IgG at 5 mg/ml.

Gyrolab™ Method

Figure 3:
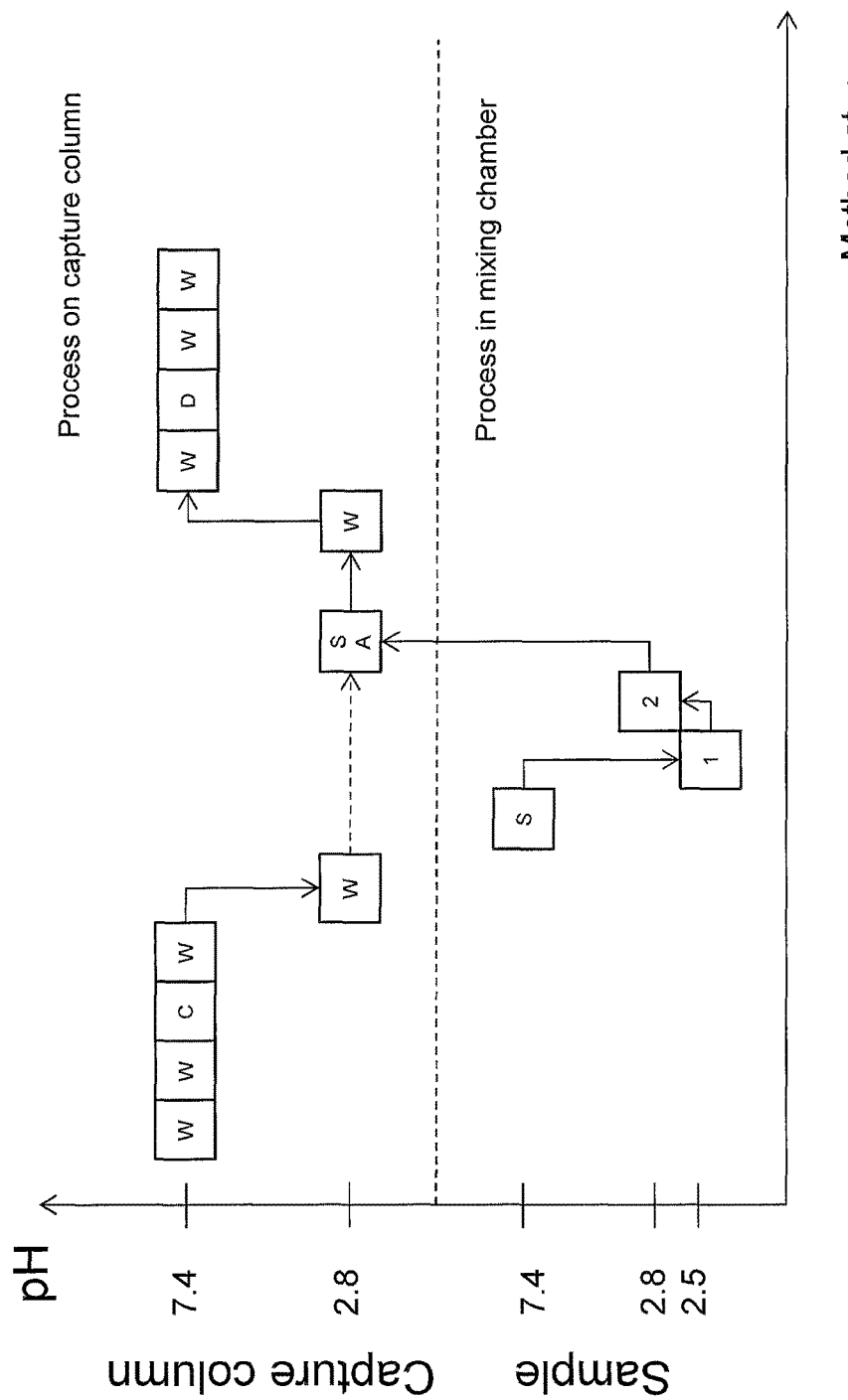
FIG. 3 is an illustration of a method for automated acid dissociation and analysis of MabSelect SuRe™ ligand in the presence of IgG at 5 mg/ml.

A method for automated acid dissociation of samples prior to analysis was developed in CDMX1. This method for automated acid dissociation and analysis of MabSelect SuRe™ ligand in the presence of IgG at 5 mg/ml is illustrated in FIG. 3, where the two panels illustrate processes on the capture column and in the sample prior to analysis. W=Column wash, C=Capture reagent, S=Sample, 1=Acid dissociation 1, 2=Acid dissociation 2, SA=Sample application on capture column, and D=Detection reagent. Arrows indicate how different process steps are interlinked.

Experiments were performed basically as outlined in FIG. 3 but using three different capture antibodies for protein A, viz. a commercial chicken polyclonal antibody, a commercial mouse monoclonal antibody, and a proprietary polyclonal antibody, respectively, varied concentrations of IgG and protein A or protein A derivative (MabSelect SuRe) in the sample as well as varied washing treatments of the capture column. The results are presented below.

Experiments

As will be described in the following, experiments performed as outlined above using CDMX1 demonstrated the principle of using separate pH's to, on the one hand, dissociate preformed protein A-IgG complexes in samples and, on the other hand, perform the immunoassay at a pH where reformation of complexes is largely prevented, and at which the capture antibody is sufficiently active in generating a dose response for MabSelect SuRe™ ligand in the presence of IgG at 5 mg/ml.

Data obtained indicate that the protein A derivative MabSelect SuRe can be determined at sub-ppm levels in concentrations of IgG at 5 mg/ml. Thus, the assay used for MabSelect SuRe spans from approximately 1 ng/ml and upwards generating a sensitivity of approximately 0.2 ppm (w/w).

Experiments using the three different capture antibodies mentioned above will now be described.

Chicken Polyclonal Anti-Protein a Antibody as Capture and Detection Antibodies (Dissociation at pH 2.5 and Capture at pH 3.5)

Mab Select SuRe

Figure 4:
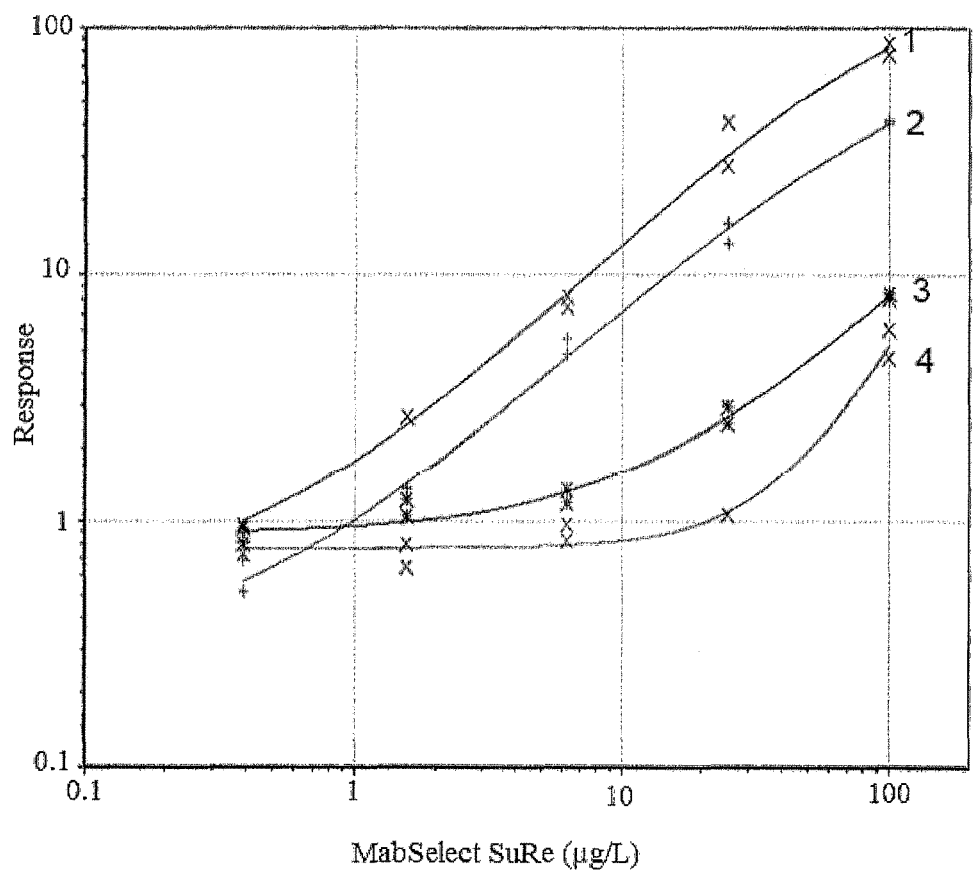
FIG. 4 is a diagram showing in overlay format dose response relationship of assaying standard curves for (1) MabSelect SuRe in buffer only; (2) Mabselect SuRe +hIgG at 5 mg/ml after processing at pH 2.5 and 3.5; (3) (control) MabSelect SuRe +5 mg/ml hIgG, dissociation at pH 2.5 and assay at pH 8.0; and (4) (control) MabSelect SuRe at 5 mg/ml of hIgG, no dissociation and assay at pH 7.4.

Early on there were indications that some minor remaining effects from presence of huge excess of IgG compared to MabSelect SuRe™ ligand afflicted recovery outcome somewhat. This is seen in FIG. 4 by comparing curves 1 and 2. FIG. 4 illustrates the dose response relationship of assaying standard curves containing MabSelect SuRe™ ligand only (1), and Mabselect SuRe+hIgG at 5 mg/ml after processing at pH 2.5 and 3.5 (2) as described for the method. As controls, standard curves of MabSelect SuRe containing 5 mg/ml hIgG were subject to dissociation at pH 2.5, but the assay was performed after neutralization at pH 8.0 (3), and finally where a standard curve (dose-response curve) of MabSelect SuRe at 5 mg/ml of hIgG was not subject to dissociation and the assay was run at pH 7.4 (4).

It was found that the above identified problem could potentially be solved by incorporating IgG in the MabSelect SuRe standard. When this was tried deviating recovery figures returned to the expected levels for most MabSelect SuRe/IgG ratios tested, as demonstrated in FIG. 5 and Table 1 below.

Figure 5:
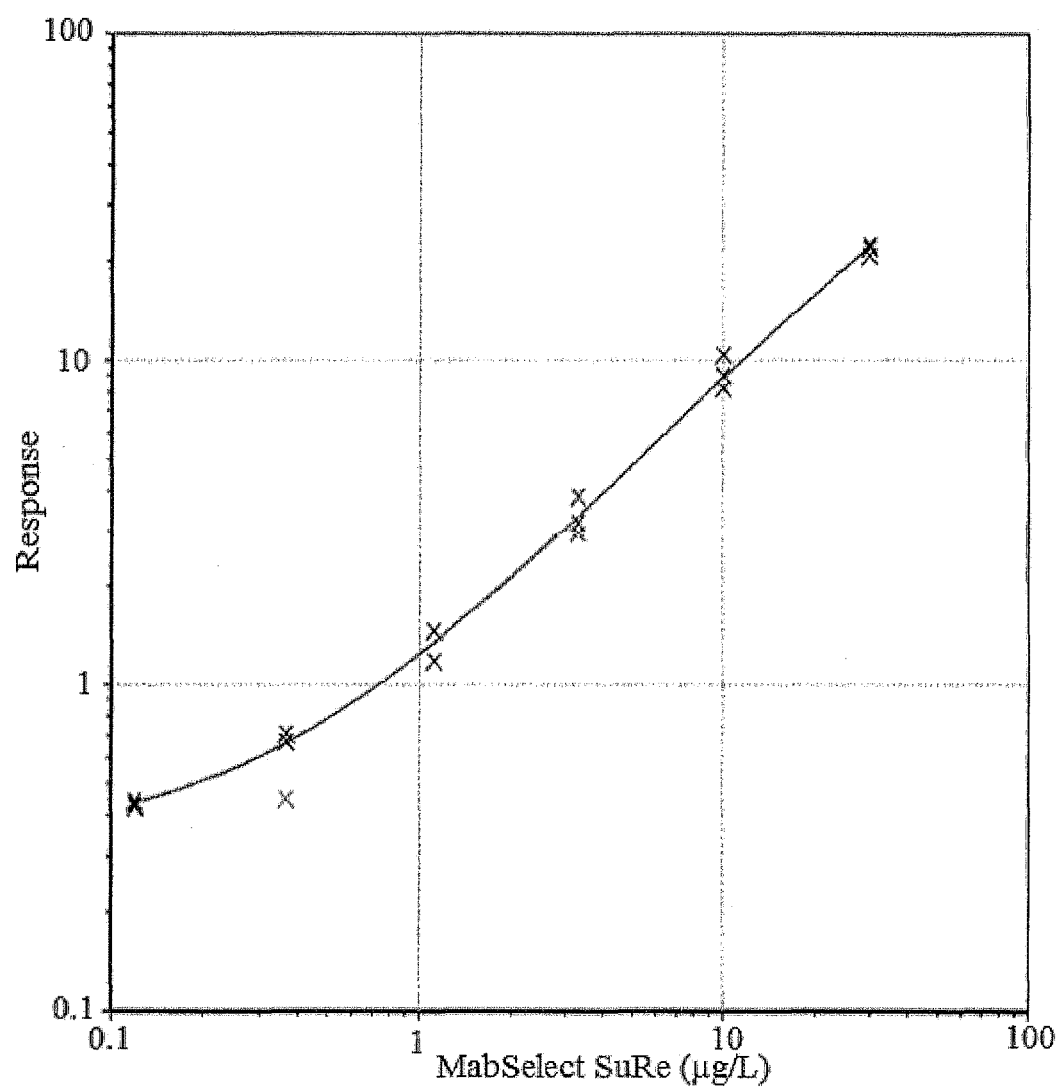
FIG. 5 is a diagram showing a standard curve of MabSelect SuRe in the presence of hIgG at 5 mg/ml.

FIG. 5 shows a standard curve of MabSelect SuRe in the presence of hIgG at 5 mg/ml. The capture column was washed prior to the capture step using a glycine-citrate buffer, pH 3.5, and further washed twice before the column was neutralized using PBS before the analytical process was finalized.

Table 1 shows the average bias of QC samples when using the standard curve in FIG. 5.

TABLE 1

| QC samples | n | IgG contents (mg/ml) | MabSelect SuRe (ng/ml) | Average Bias (%) |
|---|---|---|---|---|
| QC1 | 3 | 5 | 1 | 34.1 |
| QC2 | 3 | 5 | 2.5 | 0.3 |
| QC3 | 3 | 5 | 5 | −4.1 |
| QC4 | 3 | 5 | 10 | −0.8 |

After further modifying the method slightly, avoiding separate acidification of the capture column prior to the capture step, and using neutral pH during the first 2 washes after capture, the average bias was improved slightly, as demonstrated in FIG. 6 and Table 2 below.

Figure 6:
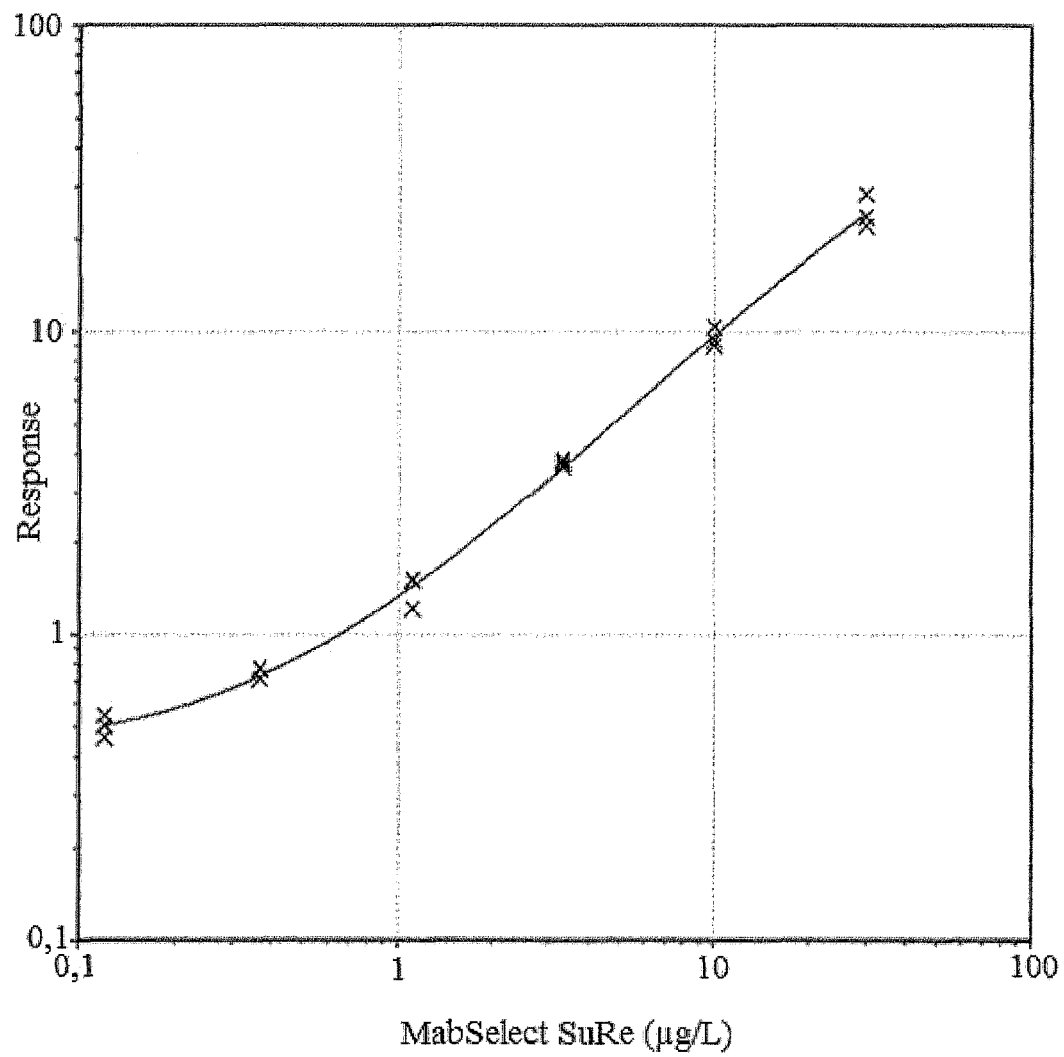
FIG. 6 is a diagram showing a standard curve for Mab Select SuRe in the presence of hIgG at 5 mg/ml.

FIG. 6 shows a dose response curve for MabSelect SuRe in presence of hIgG at 5 mg/ml. The capture column was kept in PBS, pH 7.4, during the entire process.

Table 2 shows the average bias of QC samples when using the standard curve in FIG. 6.

TABLE 2

| QC samples | n | IgG contents (mg/ml) | MabSelect SuRe (ng/ml) | Average Bias (%) |
|---|---|---|---|---|
| QC1 | 3 | 5 | 1 | 18.5 |
| QC2 | 3 | 5 | 2.5 | 0.4 |
| QC3 | 3 | 5 | 5 | −6.7 |
| QC4 | 3 | 5 | 10 | −8.5 |

Mouse Monoclonal Anti-Protein a Antibody as Capture Antibody and Chicken Polyclonal Anti-Protein a Antibody as Detection Antibody (Dissociation at pH 2.3 and Capture at pH 3.3)

Native protein A

The possibility to analyze native protein A using the same principle procedure as above was also evaluated. In this case a standard curve containing native protein A was prepared in the range of 30-0.12 ng/ml in the presence of 5 mg/ml of polyclonal human IgG. The dissociation step was performed at pH 2.3, and the analysis step at pH 3.3. In all other aspects the same principle was followed as for analysis of MabSelect SuRe ligand. Data from this experiment is shown in FIG. 7 and Table 3 below.

Figure 7:
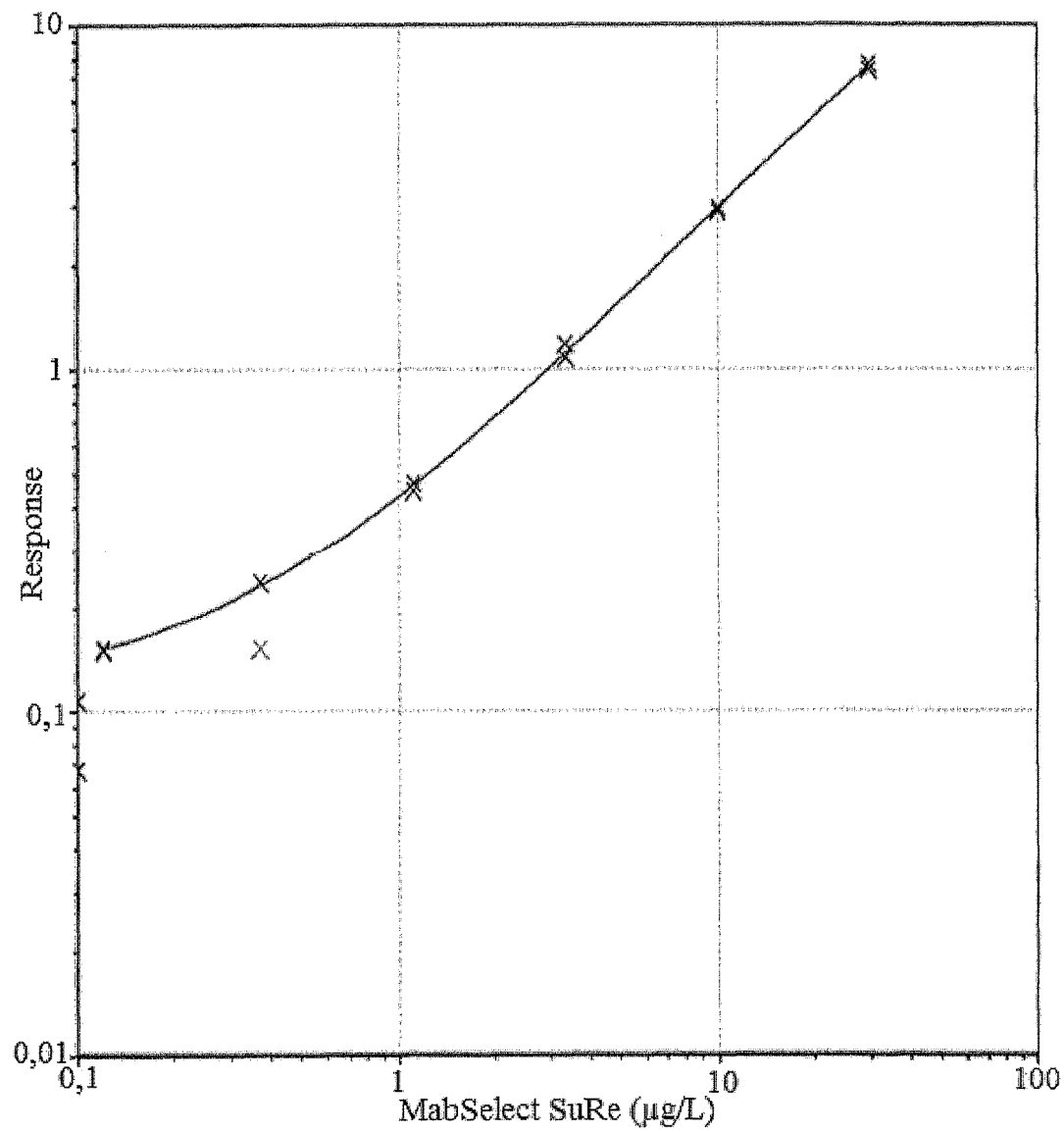
FIG. 7 is a diagram showing a standard curve for native protein A in the presence of polyclonal, human IgG at 5 mg/ml (pH for dissociation of complexes 2.3, and pH for analysis 3.3).

FIG. 7 shows a dose response curve for native protein A in the presence of polyclonal, human IgG at 5 mg/ml. The pH selected for dissociation of protein A-IgG complexes was 2.3 and the pH selected for analysis was 3.3.

Table 3 shows analysis of QC samples containing different concentrations of native protein A in the presence of polyclonal human IgG at 5 mg/ml employing dissociation at pH 2.3 and analysis at pH 3.3 in the assay. As can be seen the bias is within ±20% from protein A concentrations exceeding 2.5 ng/ml.

TABLE 3

| QC samples | n | IgG contents (mg/ml) | Protein A (ng/ml) | Average Bias (%) |
|---|---|---|---|---|
| QC1 | 3 | 5 | 1 | −70.9 |
| QC2 | 3 | 5 | 2.5 | 11.2 |
| QC3 | 3 | 5 | 5 | 8.1 |
| QC4 | 3 | 5 | 10 | −11.2 |

Proprietary Polyclonal Anti-Protein a Antibody as Capture and Detection Antibodies (Dissociation at pH 2.5 and Capture at pH 2.8)

Mab Select SuRe

Experiments basically corresponding to those described above were performed in CDMX1 using a proprietary capturing polyclonal antibody instead of the commercial chicken polyclonal antibody following the procedure as shown in FIG. 3, i.e. processing at pH 2.5 and pH 2.8, etc.

Figure 8:
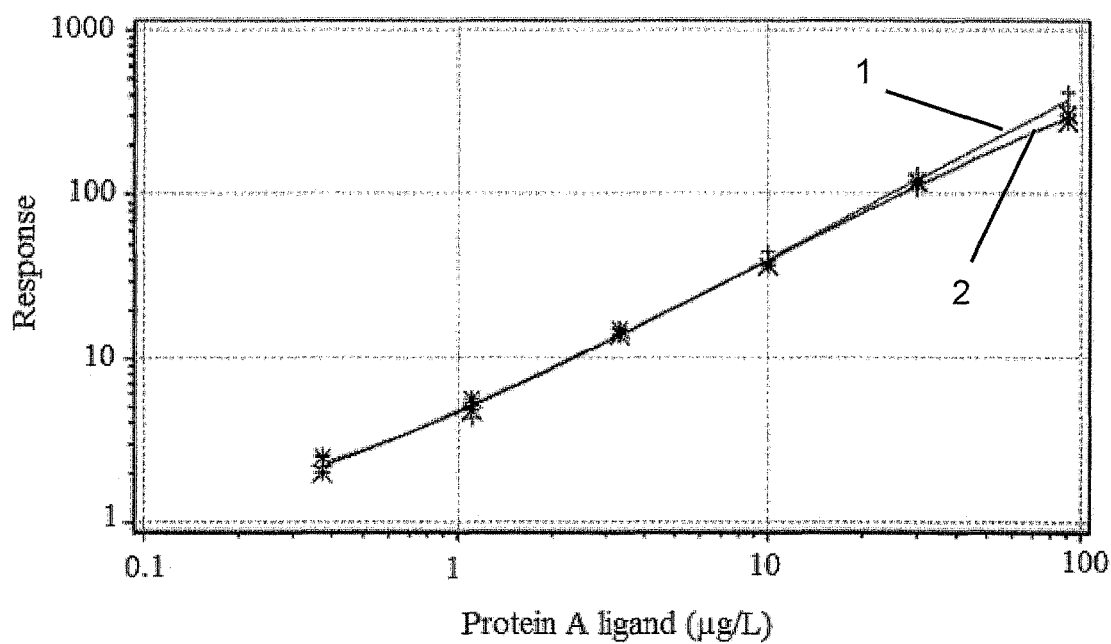
FIG. 8 is a diagram showing overlayed standard curves for two different molecular forms of protein A [native (1) and MabSelect SuRe (2)] in the presence of human polyclonal IgG (Octagam™) at a concentration of 5 mg/ml.

FIG. 8 shows an overlay chart of standard curves for (1) protein A and (2) MabSelect SuRe in the presence of human polyclonal IgG (Octagam™) at a concentration of 5 mg/ml.

Figure 9:
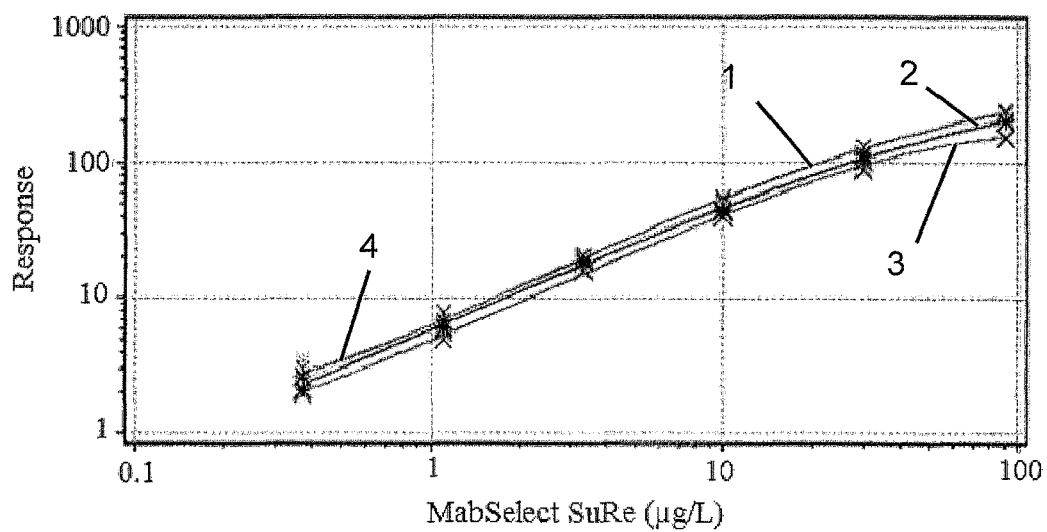
FIG. 9 is a diagram showing in overlay format standard curves for MabSelect SuRe in the presence of different concentrations of Humira™ (a therapeutic monoclonal antibody). (1) is MabSelect SuRe in buffer only; (2) is MabSelect SuRe in 10 mg per ml Humira™; (3) is MabSelect SuRe in 5 mg per ml Humira™; and (4) is MabSelect SuRe in 2 mg per ml Humira™.

FIG. 9 shows an overlay chart of standard curves for (1) MabSelect SuRe in buffer only, (2) MabSelect SuRe in 10 mg/ml Humira™ (a therapeutic monoclonal antibody), (3) MabSelect SuRe in 5 mg/ml Humira™, and (4) MabSelect SuRe in 2 mg/ml Humira™.

Using the standard curves in FIG. 9, QC samples containing different concentrations of MabSelect SuRe, prepared in different concentrations of Humira™, were analyzed for concentration of MabSelect SuRe in CDMX1. The average bias in relation to the expected concentration was determined. The results are illustrated in Table 4 below.

TABLE 4

Humira™

| | MabSelect SuRe (µg/L) | IgG contents (g/L) | n | Measured conc MabSelect SuRe (µg/L) | CV Conc (%) | Average Bias (%) |
|---|---|---|---|---|---|---|
| QC1 | 2 | 0 | 2 | 2.1 | 4.1 | 5.9 |
| | | 2 | 2 | 1.7 | 17.0 | −12.8 |
| | | 5 | 2 | 2.1 | 7.8 | 3.9 |
| | | 10 | 2 | 2.3 | 3.9 | 15.3 |
| QC2 | 5 | 0 | 2 | 4.4 | 3.4 | −11.9 |
| | | 2 | 2 | 4.3 | 3.2 | −13.8 |
| | | 5 | 2 | 5.2 | 5.6 | 4.2 |
| | | 10 | 2 | 5.9 | 9.7 | 18.1 |
| QC3 | 10 | 0 | 2 | 8.9 | 1.9 | −10.9 |
| | | 2 | 2 | 9.2 | 0.1 | −8.3 |
| | | 5 | 2 | 8.9 | 4.5 | −10.5 |
| | | 10 | 2 | 9.6 | 6.8 | −4.2 |
| QC4 | 20 | 0 | 2 | 17.7 | 9.7 | −11.7 |
| | | 2 | 2 | 15.3 | 9.3 | −23.4 |
| | | 5 | 2 | 16.8 | 8.5 | −16.0 |
| | | 10 | 2 | 19.7 | 2.1 | −1.3 |

CV = coefficient of variation

Figure 10:
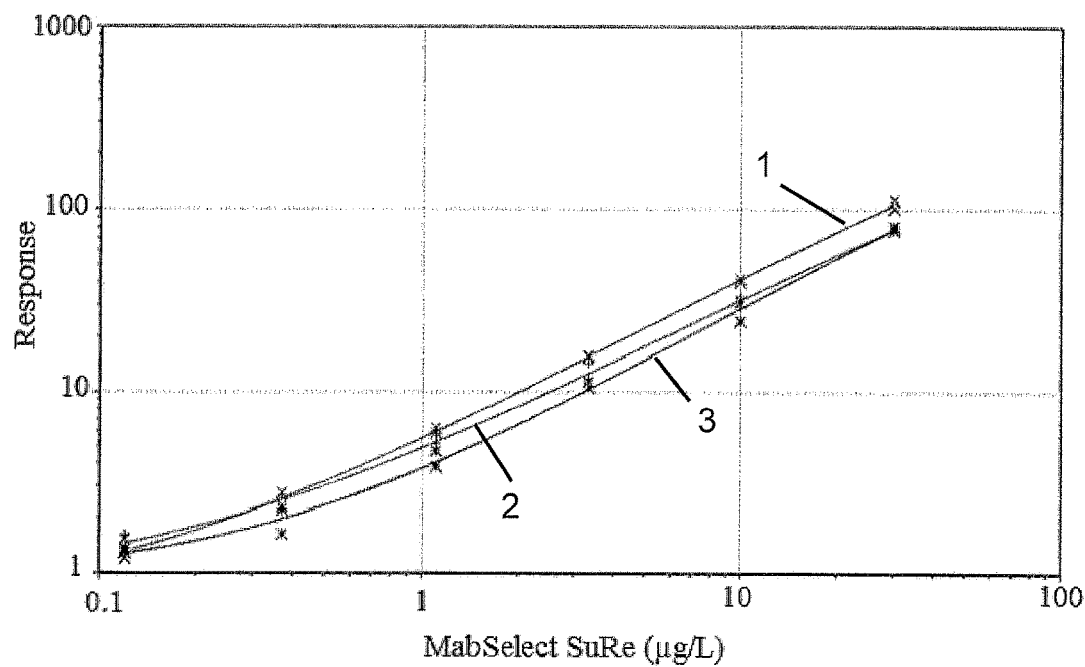
FIG. 10 is a diagram showing in overlay format standard curves for residual MabSelect SuRe (1) in buffer only; (2) in the presence of 5 mg per ml Herceptin™ (a therapeutic monoclonal antibody); and (3) in the presence of 5 mg per ml Humira™.

FIG. 10 shows an overlay chart of standard curves for residual MabSelect SuRe (1) in buffer only, (2) in the presence of 5 mg per ml Herceptin™, and (3) in the presence of 5 mg per ml Humira™.

Using the standard curves in FIG. 10, residual MabSelect SuRe in samples containing recombinant antibodies at 5 mg/ml (Herceptin™ and Humira™, respectively) were quantified. The results are presented in Table 5 below.

TABLE 5

| | | | In Buffer | | In Herceptin™ | | In Humira™ | |
|---|---|---|---|---|---|---|---|---|
| | n | IgG contents (g/L) | Measured Conc MabSelect SuRe (µg/L) | CV Conc (%) | Measured Conc MabSelect SuRe (µg/L) | CV Conc (%) | Measured Conc MabSelect SuRe (µg/L) | CV Conc (%) |
| Sample A | 2 | 5 | 2.0 | 2.5 | 1.3 | 25.8 | 2.2 | 2.2 |
| Sample B | 2 | 5 | 4.4 | 11.0 | 3.4 | 5.7 | 4.6 | 8.5 |
| Sample C | 2 | 5 | 6.5 | 1.2 | 4.7 | 1.8 | 5.3 | 0.3 |

Determination of Unknown Concentrations of MabSelect SuRe in Samples

Figure 11:
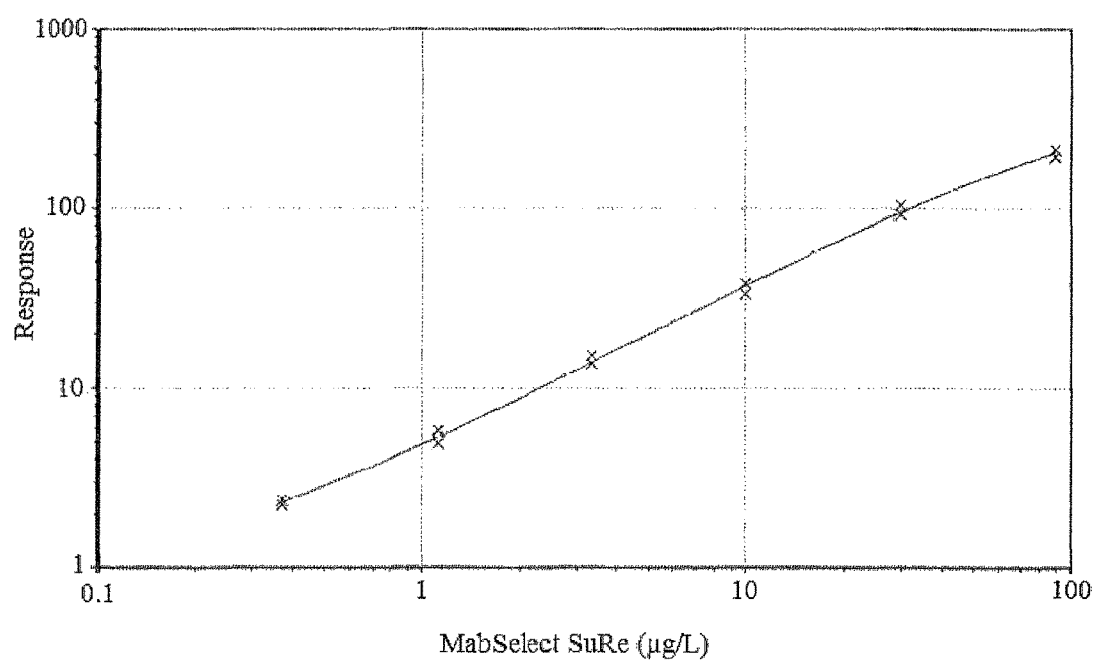
FIG. 11 is a diagram showing a standard curve for MabSelect SuRe in the presence of Humira™ at 5 mg/ml.

IgG containing (Humira™) samples contaminated with residual MabSelect SuRe were provided. Samples were first normalized by diluting them to a concentration of 5 g/L. Samples were then analyzed for protein A using the above outlined procedure involving acid dissociation at pH 2.5 and capture at pH 2.8. A standard curve for dose-response vs concentration of MabSelect SuRe was prepared as shown in FIG. 11. The concentration of residual MabSelect SuRe in the original samples were then determined using the standard curve and calculated by compensating for the dilution factor. The precision (CV %) of duplicate determinations is reported. The results are shown in Table 6 below.

TABLE 6

| | n | IgG contents (g/L) | Diluted to IgG conc (g/L) | Measured conc MabSelect SuRe compensated for dilution (µg/L) | CV Conc (%) |
|---|---|---|---|---|---|
| Sample A | 2 | 10 | 5 | 4.6 | 16.6 |
| Sample B | 2 | 10 | 5 | 17.8 | 0.4 |
| Sample C | 2 | 10 | 5 | 49.9 | 3.6 |
| Sample D | 2 | 20 | 5 | 4.6 | 17.8 |
| Sample E | 2 | 20 | 5 | 16.5 | 8.3 |
| Sample F | 2 | 20 | 5 | 55.6 | 5.7 |
| Sample G | 2 | 40 | 5 | 3.8 | 27.5 |
| Sample H | 2 | 40 | 5 | 18.5 | 10.2 |
| Sample I | 2 | 40 | 5 | 45.6 | 9.7 |

CONCLUSIONS

As demonstrated above, a fully automated, microfluidic procedure where MabSelect SuRe™ ligand, a potential leachate from affinity chromatograpy of immunoglobulins, can be accurately quantified in the presence of large concentrations of IgG, has been successfully implemented.

It has further been demonstrated that the procedure can be performed in a CD containing microfluidic structures, each having a mixing chamber upstream the capture column in which pretreatment of sample with different buffers at different pH can be performed in a standardized manner.

The procedure takes, depending on the specific set up, on average approximately one hour.

The relative concentration of MabSelect SuRe™ ligand that can be detected is in the range of 0.2-0.5 ppm at 5 mg/ml of IgG (w/w), a relative concentration that is far below the regulatory accepted level of impurity (13).

The principal dissociation and analysis procedure is also compatible with native protein A in polyclonal, human IgG at 5 mg/ml.

Kit Composition—Assay for Residual Protein A

An exemplary kit for performing analysis of residual protein A (or MabSelect SuRe) in the presence of IgG comprises the following reagents A to I. Reagents A, B and C are provided as stock solutions intended to be diluted with diluent reagents G, H and I, respectively. The entire kit is composed of nine different types of liquids sufficient for 5 Gyrolab™ ADA CDs (Gyros AB) generating 240 data points (48/CD).

Reagent A: Capture reagent, biotinylated anti-protein A antibody, 625 µg/ml.
Reagent B: Detection reagent, fluorophore labelled anti-protein A antibody, 200 nM.
Reagent C: Native Protein A, 1000 µg/L.
Reagent D: Acid Dissociation Buffer 1, 0.25 M Glycine-HCl, pH 2.5.
Reagent E: Acid Dissociation Buffer 2, 0.1 M Citrate buffer, pH 3.4.
Reagent F: Acidic Wash buffer, one part Reagent D mixed with one part Reagent E.
Reagent G (2 vials): Neutral wash buffer and for diluting capture reagent A.
Reagent H (2 vials): Sample Dilution Buffer, Rexxip™ ADA (P0020027, Gyros AB) for diluting samples.
Reagent I: Detecting Antibody Buffer, Rexxip™ F (P0004825, Gyros AB) for diluting detecting reagent B (0.5 ml)

It is to be noted that when the sample volume is 200 nl, addition of 200 nl 0.1 M Citrate buffer, pH 3.4, to a mixture of 200 nl sample and 200 nl Acid Dissociation Buffer 1 (pH 2.5) gives a resulting pH of 2.8.

The present invention is not limited to the above-described preferred embodiments. Various alternatives, modifications and equivalents may be used. Therefore, the above embodiments should not be taken as limiting the scope of the invention, which is defined by the appending claims.

REFERENCES

1. Randall Slemmon J., Meredith J., Guss V., Andreasson U., Andreasen N., Zetterberg H., Blennow K. Measurement of Ab1-42 in cerebrospinal fluid is influenced by matrix effects. J. Neurochem. 212, 325-333, 2012.
2. Murphy G., Nagase H. Progress in matrix metalloproteinase research. Mol. Aspects. Med. 29, 290-308, 2008.
3. Lindahl B., Venge P., Eggers K M., Gedeborg R., Ristiniemi N., Wittfooth S., Pettersson K. Autoantibodies to cardiac troponin in acute coronary syndromes. Clin. Chim. Acta. 411, 1793-1798, 2010.
4. Reuschenbach M., von Knebel Doeberitz M., Wentzensen N. A systematic review of humoral immune responses against tumor antigens. Cancer Immunol. Immunther. 58, 1535-1544, 2009.
5. Saurabh Aggarwal. What's fueling the biotech engine— 2010 to 2011. Nat. Biotechnol. 29, 1083-1089 doi: 10.1038/nbt.2060, 2012.
6. Chon J H., Zarbis-Papastoitsis G. Advances in the production and downsteam processing of antibodies. New Biotechnology, 28, 458-463, 2011.
7. Forsgren A, Sjöquist J. "Protein A" from Staphylococcus aureus. I. Pseudo-immune reaction with g-globulin. J. Immunol. 97, 822-827, 1966.
8. Inganäs M. Comparison of mechanisms of interaction between protein A from Staphylococcus aureus and human monoclonal IgG, IgA and IgM in relation to the classical Fcγ and alternative F(ab')$_2$ε protein A interactions. Scand. J. Immunol. 13(4), 343-52, 1981.
9. Starovasnik M A, O'Connel M P, Fairbrother W J, Kelley R F. Antibody variable region binding by Staphylococcal protein A: Thermodynamic analysis and location of the Fv binding site on the E-domain. Protein Science 8, 1423-1431, 1999.
10. Nilsson B., Moks T., Jansson B., Abrahamsén L., Elmblad A., Holmgren E., Henrichson C., Jones T A., Uhlén M. A synthetic IgG-binding domain based on staphylococcal protein A. Protein Eng. 1, 107-113, 1987.
11. Jansson B., Uhlén M., Nygren P-Å. All individual domains of staphylococcal protein A show Fab binding. FEMS Immunology and Medical Microbiology. 20, 69-78, 1998.
12. Hober S., Johansson H J. Mutant protein. US patent application publication US 2006/0194950 A1.
13. FDC Reports, The Gold Sheet, 38, 1-31, 2004.

14. Steindl F., Armbruster C., Hahn R., Armbruster C., Katinger H W D. A simple method to qauntify staphylococcal protein A in the presence of human or animal IgG in various samples. J. Immunol. Meth. 235, 61-69, 2000.
15. Zhu-Shimoni J., Gunawan F., Thomas A., Vanderlaan M., Stults J. Trace level analysis of leached protein A in bioprocess samples without interference from large excess of rhMab IgG. J. Immunol. Meth. 341, 59-67, 2009.
16. Berglund A, Inganäs M. Method for determining certain bacterial polypeptides and antibodies directed against them. U.S. Pat. No. 4,752,571, 1988.
17. van Oss C J, Absolom D R., Grossberg A L., Neumann A W. Repulsive van der Waals Forces. I. Complete Dissociation of Antigen-Antibody Complexes by Means of Negative van der Waals Forces. Immunol. Comm., 8, 11-29, 1979.

The invention claimed is:

1. A method of quantitatively determining an analyte in a fluid sample by an immunoassay comprising binding of the analyte to a ligand capable of specifically binding to the analyte, wherein at least part of the analyte is present as an analyte complex, and wherein the method comprises the steps of:
   a) subjecting the sample to a first acidic pH in the range from about 1.5 to about 3.2 to at least substantially dissociate any analyte complex present and provide substantially all analyte in free form,
   b) raising the first acidic pH to a second acidic pH in the range from about 2.7 to about 4.5 where re-formation of complexes is prevented but where binding of analyte to the ligand is permitted, and
   c) detecting the binding of analyte to the ligand to quantitatively determine the analyte in the sample, wherein the analyte is selected from the group consisting of protein A, protein G, protein A/G, protein L and derivatives thereof, wherein the sample contains IgG, or an active fragment thereof, and wherein the ligand is an antibody or an active fragment thereof.

2. The method according to claim 1, wherein the ligand is immobilized to a solid support.

3. The method according to claim 1, wherein the second acidic pH is selected in the range from about 2.8 to about 4.5.

4. The method according to claim 3, wherein the first acidic pH is selected in the range of from about 2.3 to about 2.5 and/or the second acidic pH is selected in the range of from about 2.8 to about 3.2.

5. The method according to claim 1, wherein the second acidic pH is selected in the range of from about 3.0 to about 3.2.

6. The method according to claim 1, which comprises using a standard curve of response versus analyte concentration when determining the analyte concentration, wherein the standard curve is prepared using samples containing analyte and at least one species capable of complexing with the analyte.

7. The method according to claim 1, wherein the method is performed in a microfluidic system.

8. The method according to claim 7, wherein the microfluidic system is contained in a spinnable disc, and wherein fluid transport may be accomplished by centrifugal force.

9. The method of claim 1, wherein a kit, comprising:
   a detection reagent capable of binding to the analyte,
   a first acidic buffer having a pH in the range from about 1.5 to about 3.2, and
   a second acidic buffer having a pH in the range from about 2.7 to about 4.5, is used for performing steps a) to c) of said method.

10. The method according to claim 9, wherein the analyte is capable of binding to a ligand immobilized to a solid phase, and wherein the kit further comprises a capture reagent as a ligand for the analyte, wherein the capture reagent is capable of binding to the solid phase.

11. The method according to claim 9, wherein the capture reagent is biotinylated and the ligand comprises avidin or streptavidin.

12. The method according to claim 10, wherein the capture reagent is biotinylated and the ligand comprises avidin or streptavidin.

* * * * *